US012653423B1

(12) United States Patent
Mandai et al.

(10) Patent No.: US 12,653,423 B1
(45) Date of Patent: \*Jun. 16, 2026

(54) MULTI-MODE SENSOR FOR OBJECT IDENTIFICATION

(71) Applicant: Apple Inc., Cupertino, CA (US)

(72) Inventors: Shingo Mandai, Mountain View, CA (US); Vyshakh Sanjeev, San Francisco, CA (US); Andrew T. Herrington, San Francisco, CA (US); Cristiano L. Niclass, San Jose, CA (US); Scott T. Smith, San Jose, CA (US); Bernhard Buettgen, San Jose, CA (US)

(73) Assignee: Apple Inc., Cupertino, CA (US)

(\*) Notice: Subject to any disclaimer, the term of this patent is extended or adjusted under 35 U.S.C. 154(b) by 0 days.

This patent is subject to a terminal disclaimer.

(21) Appl. No.: 18/759,241

(22) Filed: Jun. 28, 2024

Related U.S. Application Data

(60) Provisional application No. 63/579,008, filed on Aug. 27, 2023.

(51) Int. Cl.
*A61B 5/1171* (2016.01)
*A61B 5/026* (2006.01)
(Continued)

(52) U.S. Cl.
CPC .......... *A61B 5/1176* (2013.01); *A61B 5/0261* (2013.01); *G01S 7/4816* (2013.01);
(Continued)

(58) Field of Classification Search
CPC .. A61B 5/0261; A61B 5/1176; G06V 10/141; G06V 2201/03; G06V 40/14;
(Continued)

(56) References Cited

U.S. PATENT DOCUMENTS

| | | | |
|---|---|---|---|
| 4,608,599 | A | 8/1986 | Kaneko et al. |
| 6,424,407 | B1 | 7/2002 | Kinrot et al. |

(Continued)

FOREIGN PATENT DOCUMENTS

| | | |
|---|---|---|
| CN | 109541619 A | 3/2019 |
| CN | 115605774 A | 1/2023 |

(Continued)

OTHER PUBLICATIONS

Wang, "Investigation of New Concepts and Solutions for Silicon Nanophotonics," Doctoral Thesis in Microelectronics and Applied Physics, Stockholm, Sweden, pp. 1-91, year 2010.
(Continued)

*Primary Examiner* — Peet Dhillon
(74) *Attorney, Agent, or Firm* — Meitar Patents LTD.; Daniel Kligler

(57) ABSTRACT

Optical sensing apparatus includes a transmitter, which transmits outgoing FM coherent optical radiation toward a target scene, and a receiver, including an array of detectors, which output electrical signals in response to photons that are incident on the detectors, and optics to image the target scene onto the array while diverting a part of the outgoing FM coherent optical radiation to form a local beam, which mixes with incoming optical radiation from the target scene. Processing circuitry processes the electrical signals output by the detectors to produce a 2D image of the target scene, to identify an object of interest in the 2D image, which is imaged onto an area within the array, to extract beat frequencies in response to the mixed optical radiation from the electrical signals output by the detectors in the area, and to measure a feature of the object of interest responsively to the beat frequencies.

17 Claims, 4 Drawing Sheets

(51) Int. Cl.

| | |
|---|---|
| *G01S 7/481* | (2006.01) |
| *G01S 17/89* | (2020.01) |
| *G06V 10/141* | (2022.01) |
| *G06V 20/64* | (2022.01) |
| *G06V 40/10* | (2022.01) |
| *G06V 40/14* | (2022.01) |
| *G06V 40/16* | (2022.01) |
| *G06V 40/70* | (2022.01) |
| *H04N 25/773* | (2023.01) |

(52) U.S. Cl.
CPC ............ *G01S 17/89* (2013.01); *G06V 10/141* (2022.01); *G06V 20/64* (2022.01); *G06V 40/14* (2022.01); *G06V 40/15* (2022.01); *G06V 40/172* (2022.01); *G06V 40/70* (2022.01); *H04N 25/773* (2023.01); *G06V 2201/03* (2022.01)

(58) Field of Classification Search
CPC ...... G06V 40/15; G06V 40/70; G06V 40/172; G06V 20/64; H04N 25/773; G01S 7/4816; G01S 17/89
See application file for complete search history.

(56) References Cited

U.S. PATENT DOCUMENTS

| | | | |
|---|---|---|---|
| 8,493,496 | B2 | 7/2013 | Freedman et al. |
| 9,525,863 | B2 | 12/2016 | Nawasra et al. |
| 9,529,079 | B1 | 12/2016 | Droz et al. |
| 9,971,948 | B1 | 5/2018 | Herrington et al. |
| 10,018,723 | B2 | 7/2018 | Sromin et al. |
| 10,908,267 | B1 | 2/2021 | Gagne et al. |
| 2006/0227316 | A1 | 10/2006 | Gatt |
| 2009/0216093 | A1* | 8/2009 | Sebastian .............. A61B 5/1113 600/301 |
| 2013/0206963 | A1 | 8/2013 | Grund |
| 2013/0207970 | A1 | 8/2013 | Shpunt et al. |
| 2013/0208258 | A1 | 8/2013 | Eisele et al. |
| 2015/0261946 | A1 | 9/2015 | Yoon et al. |
| 2017/0172510 | A1* | 6/2017 | Homyk ................ A61B 5/7285 |
| 2017/0285325 | A1 | 10/2017 | Erlich et al. |
| 2017/0299698 | A1 | 10/2017 | Yagi et al. |
| 2017/0322015 | A1 | 11/2017 | Knüttel |
| 2019/0025426 | A1 | 1/2019 | Satyan et al. |
| 2019/0036308 | A1 | 1/2019 | Carson et al. |
| 2020/0234785 | A1 | 7/2020 | Kyselov et al. |
| 2020/0257128 | A1 | 8/2020 | Sakai et al. |
| 2021/0031119 | A1 | 2/2021 | Clements |
| 2021/0109197 | A1* | 4/2021 | O'Keeffe .............. G01S 7/4816 |
| 2021/0165083 | A1* | 6/2021 | Fine ...................... G01S 7/4863 |
| 2021/0257396 | A1 | 8/2021 | Piggott et al. |
| 2021/0314734 | A1 | 10/2021 | Mehta et al. |
| 2021/0341611 | A1 | 11/2021 | Boloorian |
| 2021/0373350 | A1 | 12/2021 | Oda et al. |
| 2021/0382153 | A1 | 12/2021 | Dielacher et al. |
| 2021/0405164 | A1 | 12/2021 | Klemme et al. |
| 2022/0043108 | A1 | 2/2022 | Lavian |
| 2022/0050201 | A1 | 2/2022 | Sun et al. |
| 2022/0075076 | A1 | 3/2022 | Michaels et al. |
| 2022/0091242 | A1 | 3/2022 | Gagne et al. |
| 2022/0113379 | A1 | 4/2022 | Viswanatha et al. |
| 2022/0137226 | A1* | 5/2022 | Kim ...................... G06V 20/64 348/46 |
| 2022/0187457 | A1 | 6/2022 | Daami et al. |
| 2022/0187471 | A1* | 6/2022 | Eshel ...................... G01S 17/89 |
| 2022/0404475 | A1 | 12/2022 | Laflaquiere et al. |
| 2023/0366986 | A1 | 11/2023 | Islam et al. |
| 2023/0393241 | A1* | 12/2023 | Gutierrez Barragan ..................... G01S 7/487 |
| 2023/0400582 | A1 | 12/2023 | Cohen |
| 2024/0004045 | A1 | 1/2024 | Shnaiderman et al. |
| 2024/0045146 | A1 | 2/2024 | Islam et al. |
| 2024/0069285 | A1 | 2/2024 | Hajati et al. |
| 2024/0288549 | A1 | 8/2024 | Oggier et al. |
| 2024/0288552 | A1* | 8/2024 | Milgrome .............. G01S 7/497 |
| 2024/0369689 | A1 | 11/2024 | Hajati et al. |
| 2025/0116763 | A1 | 4/2025 | Spollard et al. |

FOREIGN PATENT DOCUMENTS

| | | | |
|---|---|---|---|
| CN | 115932888 | A | 4/2023 |
| DE | 102020213161 | A1 | 4/2022 |
| EP | 3961257 | A1 | 3/2022 |
| EP | 3971614 | A1 | 3/2022 |
| ES | 2896302 | T3 | 2/2022 |
| WO | 2008084929 | A1 | 7/2008 |
| WO | 2015098288 | A1 | 7/2015 |
| WO | 2018102190 | A1 | 6/2018 |
| WO | 2019036383 | A1 | 2/2019 |
| WO | 2020161260 | A1 | 8/2020 |
| WO | 2020190338 | A1 | 9/2020 |
| WO | 2022168500 | A1 | 8/2022 |
| WO | 2023012527 | A1 | 2/2023 |

OTHER PUBLICATIONS

Sacher et al., "Wide Bandwidth and High Coupling Efficiency Si3N4-on-SOI Dual-level Grating Coupler," Optics Express, vol. 22, No. 9, pp. 1-10, May 5, 2014.

Rogers et al., "A Universal 3D Imaging Sensor on a Silicon Photonics Platform," ArXiv:2008.02411v3, pp. 1-18, Nov. 11, 2020.

Lumerical Inc., "Tutorial—Splitter Optimization," pp. 1-8, year 2019, as downloaded from https://lumopt.readthedocs.io/en/latest/tutorial.html.

Nicolaescu et al., "3D Imaging via Silicon-photonics-based LIDAR," Proc. SPIE vol. 11691, Silicon Photonics XVI, pp. 1-12, year 2021.

Marchetti et al., "Coupling Strategies for Silicon Photonics Integrated Chips [Invited]," Photonics Reseach, vol. 7, No. 2, pp. 1-39, Feb. 2019.

Marchetti et al., "High-efficiency Grating-couplers: Demonstration of a New Design Strategy," Springer Nature, Scientific Reports, vol. 7, pp. 1-9, Nov. 2017.

Hooten et al., "Inverse Design of Grating Couplers Using the Policy Gradient Method from Reinforcement Learning," De Gruyter, Nanophotonics, vol. 10, issue 15, pp. 3843-3856, year 2021.

Michaels, "A Hierarchical Approach to the Design and Optimization of Photonics," PhD Thesis, University of California, Berkeley, pp. 1-139, year 2019.

Molesky, "Outlook for Inverse Design in Nanophotonics," arXiv:1801.06715v1, pp. 1-13, Jan. 20, 2018.

Vasilyev, "The Optoelectronic Swept-Frequency Laser and Its Applications in Ranging, Three-Dimensional Imaging, and Coherent Beam Combining of Chirped-Seed Amplifiers," Doctoral Thesis, California Institute of Technology, pp. 1-177, year 2013.

Mandai et al., U.S. Appl. No. 18/623,080, filed Apr. 1, 2024.

Kamali et al., "A review of dielectric optical metasurfaces for wavefront control," Nanophotonics, Open Access, pp. 1-84, May 18, 2018.

Xiong et al., "Controlling the degrees of freedom in metasurface designs for multi-functional optical devices," Nanoscale Advances, vol. 1, pp. 3786-3806, year 2019.

Wikipedia, "Laser speckle contrast imaging," pp. 1-8, last edited Dec. 12, 2023.

Li et al., "Transmissive-detected laser speckle contrast imaging for blood flow monitoring in thick tissue: , from Monte Carlo simulation to experimental demonstration," Nature, Light: Science & Applications, vol. 10, article No. 241, pp. 1-43, Dec. 3, 2021.

Heeman et al., "Clinical applications of laser speckle contrast imaging: a review," Journal of Biomedical Optics, vol. 24, No. 8, pp. 080901-1-80901-11, Aug. 2019.

Zalevsky et al., "Simultaneous remote extraction of multiple speech sources and heart beats from secondary speckles pattern," Optics Express, vol. 17, No. 24, pp. 1-15, Nov. 23, 2009.

Ding et al., "Compensation of Laser Frequency Tuning Nonlinearity of a Long Range OFDR Using Deskew Filter," Optics Express, vol. 21, No. 3, pp. 3826-3834, Feb. 11, 2013.

(56)    References Cited

OTHER PUBLICATIONS

Du et al., "Method for Improving Spatial Resolution and Amplitude by Optimized Deskew Filter in Long-Range OFDR," IEEE Photonics Journal, vol. 6, No. 5, pp. 1-13, Oct. 2014.

Sandborn, "FMCW Lidar: Scaling to the Chip-Level and Improving Phase-Noise-Limited Performance," Dissertation, Electrical Engineering and Computer Sciences, University of California at Berkeley, USA, pp. 1-90, Dec. 1, 2019.

Meta et al., "Signal Processing for FMCW SAR," IEEE Transactions on Geoscience and Remote Sensing, vol. 45, No. 11, pp. 3519-3532, Nov. 2007.

Peek, "Estimation and Compensation of Frequency Sweep Nonlinearity in FMCW Radar," M.Sc. thesis in Applied Mathematics, The University of Twente, The Netherlands, pp. 1-67, Sep. 2011.

Meta et al., "Range Non-Linearities Correction in FMCW SAR," IEEE, pp. 403-406, year 2006.

Baumann et al., "Speckle Phase Noise in Coherent Laser Ranging: Fundamental Precision Limitations," Optics Letters, vol. 39, issue 16, pp. 4776-4779, Aug. 15, 2014.

Islam et al., U.S. Appl. No. 17/577,039, filed Jan. 17, 2022.

Islam et al., U.S. Appl. No. 17/742,419, filed May 12, 2022.

Northcott et al., U.S. Appl. No. 18/094,999, filed Jan. 10, 2023.

Shnaiderman et al., U.S. Appl. No. 18/094,997, filed Jan. 10, 2023.

Axelrod et al., "Reconfigurabe Quasi-Resonance Scanner for 3D FMCW Imaging," Optics Letters, vol. 39, issue 16, pp. 4776-4779, year 2014.

Kendrisic et al., "Thermally Tuned VCSEL-Based SS-OCT System," Biophotonics Congress: Biomedical Optics (Translational, Microscopy, OCT, OTS, BRAIN), Optica Publishing Group, pp. 1-2, year 2022.

Non-Final Office Action U.S. Appl. No. 17/863,419, dated Aug. 12, 2025.

Huang, Frequency-modulated continuous-wave 3D imaging with high photon efficiency Huang, Jul. 12, 2022, vol. 47, pp. 3568-3571.

Non-Final Office Action, U.S. Appl. No. 18/759,249, Dated Jul. 23, 2025.

Japanese Office Action, Application # 2024-115446, dated Jun. 2, 2025.

Japanese Office Action, Application # 2024-115446, dated Oct. 14, 2025.

Non Final Office Action U.S. Appl. No. 17/838,217, dated Jul. 30, 2025.

Ma et al, "Self-Supervised Sparse-to-Dense: Self-Supervised Depth Completion from LiDAR and Monocular Camera", 2019 International Conference on Robotics and Automation(ICRA), Aug. 12, 2019, pp. 1-12.

Non-Final Office Action. Application U.S. Appl. No. 17/742,419, dated Jun. 6, 2025.

Second Office Action (CNIPA) for Application # 202180031211.X, dated Jun. 7, 2025.

* cited by examiner

MULTI-MODE SENSOR FOR OBJECT IDENTIFICATION

CROSS-REFERENCE TO RELATED APPLICATION

This patent application claims the benefit of U.S. Provisional Patent Application 63/579,008, filed Aug. 27, 2023. This application is also related to U.S. patent application Ser. No. 18/623,080, filed Apr. 1, 2024. The disclosures of both these related applications are incorporated herein by reference.

FIELD

The present invention relates generally to systems and methods for optical sensing, and particularly to optical object identification.

BACKGROUND

In frequency-modulated continuous-wave (FMCW) LiDAR sensing arrangements, a radio-frequency (RF) chirp is applied to modulate the frequency of a beam of optical radiation (typically a single-mode laser beam) that is directed toward a target. The optical radiation reflected from the target is mixed with a sample of the transmitted light, referred to as a "local oscillator" or "local beam." The mixed optical radiation is detected by a photodetector, such as a balanced photodiode pair, which then outputs an RF signal comprising a beat frequency that is proportional to the distance to the target. When the target is moving, the resulting Doppler shift of the reflected optical radiation will cause the beat frequency to increase or decrease, depending on the direction of motion.

By comparing the beat frequencies obtained from chirps of positive and negative slopes, it is thus possible to extract both the range and the velocity of the target. In the ideal case, if the beat frequency due to the Doppler shift is d, and the beat frequency due to the chirp and range is r, then the measured beat frequency for the up-chirp will be $f_u = d+r$, and the beat frequency on the down-chirp will be $f_d = r-d$. Thus, the difference between the measured up and down chirp frequencies reveals the Doppler shift, and the sum the range.

The terms "light" and "optical radiation," as used in the context of the present description and in the claims, refer to electromagnetic radiation in any of the visible, ultraviolet, and infrared spectral bands.

A wide variety of methods are known in the art for optical identification of faces. Some of these methods are based on analysis of a two-dimensional (2D) image of the face, while others use three-dimensional (3D) information, such as a depth map of the face created by 3D optical sensing techniques. Other techniques identify anatomical structures such as blood vessels. For example, U.S. Pat. No. 9,971,948 describes apparatus including an image capture device, which includes an optical transmitter configured to emit one or more pulses of infrared radiation toward an area containing a body surface of a living subject, and an optical receiver, which receives the pulses reflected from the body surface and generates an output indicative of a modulation of the pulses by tissue below the body surface. A processor generates, based on the modulation of the pulses, an image of blood vessels located beneath the body surface within the area.

SUMMARY

Embodiments of the present invention that are described hereinbelow provide improved apparatus and methods for optical sensing.

There is therefore provided, in accordance with an embodiment of the invention, optical sensing apparatus, including a transmitter, which is configured to transmit outgoing frequency-modulated (FM) coherent optical radiation toward a target scene, and a receiver, including an array of detectors, which are configured to output electrical signals in response to photons that are incident on the detectors, and optics configured to image the target scene onto the array while diverting a part of the outgoing FM coherent optical radiation to form a local beam, which mixes with incoming optical radiation from the target scene. Processing circuitry is configured to process the electrical signals output by the detectors to produce a two-dimensional (2D) image of the target scene, to identify an object of interest in the 2D image, which is imaged onto an area within the array, to extract beat frequencies in response to the mixed optical radiation from the electrical signals output by the detectors in the area, and to measure a feature of the object of interest responsively to the beat frequencies.

In a disclosed embodiment, the transmitter is configured to project the FM coherent optical radiation as flood radiation over a region of the target scene.

In some embodiments, the detectors are single-photon detectors, which are configured to output electrical pulses in response to the incident photons, and the processing circuitry is configured to compute counts of the electrical pulses output as a function of time by the single-photon detectors. In a disclosed embodiment, the processing circuitry is configured to produce the 2D image responsively to total counts of the electrical pulses output by each of the single-photon detectors during a given exposure time. Additionally or alternatively, the counts of the electrical pulses as the function of time define temporal waveforms, and the processing circuitry is configured to extract the beat frequencies by processing the temporal waveforms. In one embodiment, the processing circuitry is configured to select groups of the single-photon detectors within the area and to compute the counts as collective counts of the electrical pulses output by each of the selected groups of the single-photon detectors. In a disclosed embodiment, the single-photon detectors include single-photon avalanche diodes (SPADs).

In some embodiments, the transmitter is configured to apply a frequency chirp to the outgoing coherent optical radiation, and the processing circuitry is configured to measure a three-dimensional shape of the object of interest based on the beat signals that arise due to the frequency chirp.

Additionally or alternatively, the processing circuitry is configured to detect, based on the beat signals, a Doppler indicative of movement of a feature of the object of interest. In one embodiment, the object of interest is a part of a living body, and the processing circuitry is configured to detect the Doppler shift due to flow of blood in blood vessels in the living body and to identify the blood vessels responsively to the detected Doppler shift.

In another embodiment, the processing circuitry is configured to identify a face in the 2D image and to generate a three-dimensional (3D) map of the face based on the beat frequencies. In a disclosed embodiment, the processing circuitry is configured to apply the 3D map in verifying an identity of a person whose face appears in the 2D image.

There is also provided, in accordance with an embodiment of the invention, a method for optical sensing, which includes transmitting outgoing frequency-modulated (FM) coherent optical radiation toward a target scene. The target scene is imaged onto an array of detectors, which output electrical signals in response to photons that are incident on the detectors, while diverting a part of the outgoing FM coherent optical radiation to form a local beam, which mixes on the array of detectors with incoming optical radiation from the target scene. The electrical signals output by the detectors are processed to produce a two-dimensional (2D) image of the target scene. An object of interest, which is imaged onto an area within the array, is identified in the 2D image. Beat frequencies are extracted in response to the mixed optical radiation from the electrical signals output by the detectors in the area. A feature of the object of interest is measured responsively to the beat frequencies.

The present invention will be more fully understood from the following detailed description of the embodiments thereof, taken together with the drawings in which:

DETAILED DESCRIPTION

Overview

Figure 1:
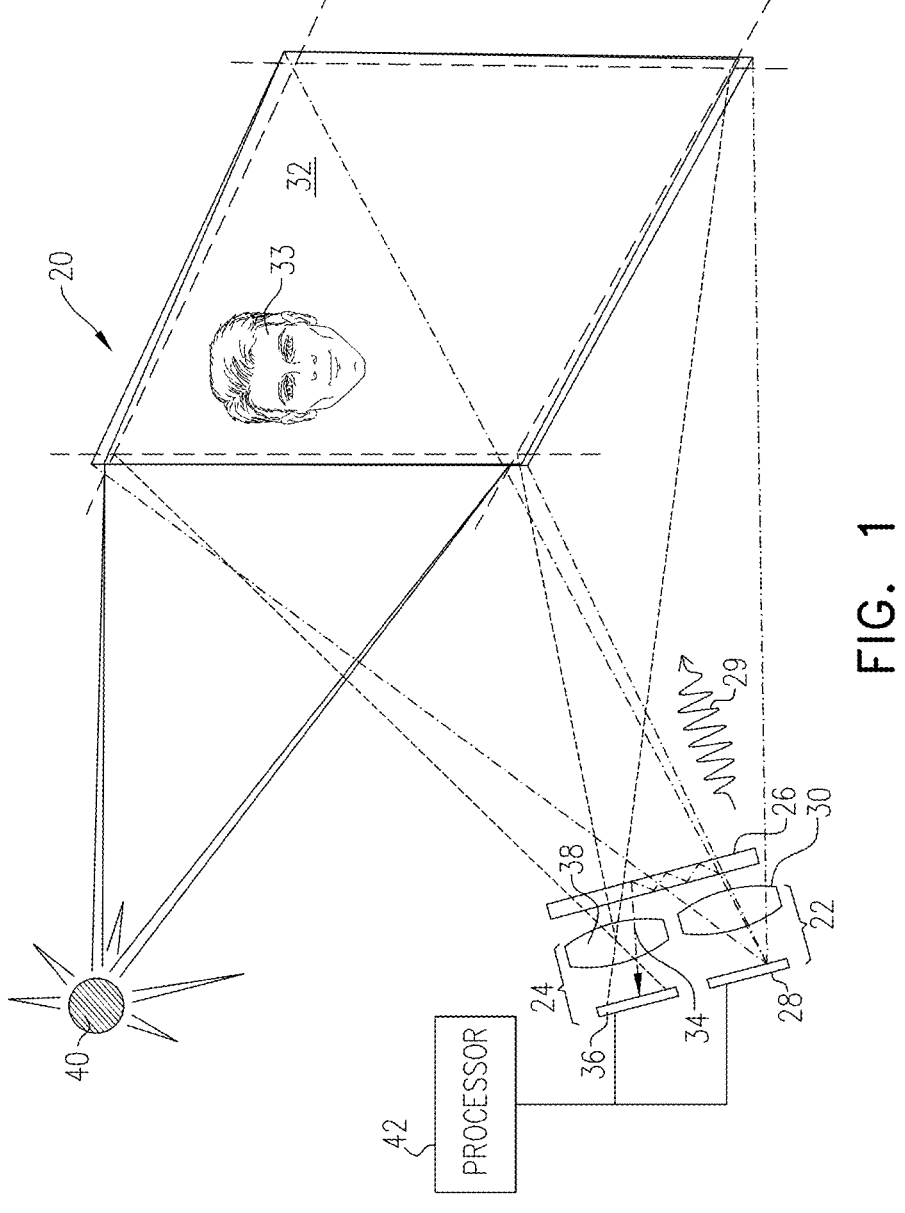
FIG. 1 is a schematic pictorial view of an optical sensing apparatus, configured to operate as part of a LiDAR system, in accordance with an embodiment of the invention.

Image-based identification is widely used in authentication applications, for example to authenticate the user of a mobile device or to control access to restricted areas and functionalities. Many authentication applications use face recognition, based on analysis of 2D video images. Such approaches, however, are prone to spoofing by presenting the camera with a picture of the face of an authorized user. More robust approaches use 3D mapping of the face; but existing 3D sensors are costly and add hardware complexity to the identification module.

Embodiments of the present invention that are described herein address this problem using a single optical transmitter and detector array to capture both a 2D image of a target scene and additional identifying features of an object of interest in the target scene. For this purpose, the disclosed embodiments provide optical sensing apparatus including a transmitter, which transmits outgoing FMCW coherent optical radiation toward the target scene, for example as flood radiation covering a region of the target scene. A receiver comprises an array of detectors, which output electrical signals in response to photons that are incident on the detectors. In some embodiments, the detectors are single-photon detectors, such as single-photon avalanche diodes (SPADs), which output electrical pulses in response to incident photons. Optics image the target scene onto the array while diverting a part of the outgoing FMCW coherent optical radiation to form a local beam, which mixes with incoming optical radiation from the target scene.

Processing circuitry processes the electrical signals output by the detectors to extract two complementary types of information: The processing circuitry produces a two-dimensional (2D) image of the target scene and identifies an object of interest in the 2D image, such as the face of a subject who is to be authenticated. The processing circuitry also processes the electrical signals that are output by the detectors in the area of the array onto which the object of interest is imaged to extract beat frequencies arising due to the mixed local beam and incoming radiation. To reduce the use of processing resources and power consumption, the processing circuit may desirably process the signals and extract the beat signals only from the detectors in this specific area of the array. The processing circuitry measures a feature of the object of interest responsively to the beat frequencies.

In some embodiments, the optical transmitter applies a frequency chirp to the outgoing coherent optical radiation and measures a 3D shape of the object of interest using FMCW detection and processing techniques. In other embodiments, the processing circuitry detects, based on the beat signals, a Doppler shift indicative of movement of a feature of the object of interest, for example the Doppler shift due to flow of blood in blood vessels in the living body. The locations at which the Doppler shift occurs can be used to identify the blood vessels. In either case, the features measured based on the beat frequencies can be used together with the 2D image in verifying the identity of a person whose face appears in the 2D image. Additionally or alternatively, the disclosed techniques can be used in other authentication and sensing applications, such as enhancing anti-spoofing performance of optical touch ID sensing devices and remote sensing of physiological parameters.

System Description

FIG. 1 is a schematic pictorial view of an optical sensing apparatus 20, in use in a face identification application in accordance with an embodiment of the invention. The apparatus comprises a transmitter (Tx) 22 and a receiver (Rx) 24, which are contained in an enclosure (not shown) with a cover glass (CG) 26.

Transmitter 22 comprises a modulated laser source 28 including suitable drive circuits, along with optics 30. The transmitter transmits outgoing FMCW coherent optical radiation 29 as flood radiation, extending over an entire field of view (FOV) 32 of the apparatus in a target scene. In the present example, the FOV contains a face 33, for example the face of a user who is to be authenticated. A small part of the transmitted radiation is diverted by cover glass 26 to form a local beam 34, which is incident on receiver 24. In the pictured examples, local beam 34 is guided within cover glass 26 to the receiver. Alternatively, the local beam may be diverted toward the receiver from other optical elements or surfaces in the apparatus, or it may be separated from the outgoing radiation by a dedicated optical surface or light guide.

Receiver 24 comprises an array 36 of SPADS, as described in greater detail hereinbelow. An objective lens 38 images the part of the target scene that is within FOV 32 of the apparatus onto SPAD array 36. The incoming optical radiation from the target scene is mixed by the optics with the local beam, and the mixed radiation is incident on the SPADs in array 36. Interference between the FM coherent radiation reflected from the target scene and the FM local beam gives rise to an optical beat signal at the SPAD array. Photons of ambient radiation (represented by a light source 40 in the upper part of the figure) that is reflected from FOV

32 will also cause the SPADs to output electrical pulses, but without any distinct beat frequency.

A processor 42 controls the operation of transmitter 22 and receiver 24 and also receives the digital waveforms corresponding to the counts of SPAD pulses that are output by the receiver. Processor 42 extracts the beat frequencies from the digital waveform generated by each pixel of SPAD array 36 and uses the beat frequency at each pixel in measuring the range from the apparatus to a point in the target scene that is imaged onto the pixel. (A "pixel" may comprise a single SPAD or a group of neighboring SPADs, as described further hereinbelow.) Processor 42 may also compute velocities of the points in the target scene based on the up-chirp and down-chirp beat frequencies, as explained above. The processor typically comprises a programmable microprocessor or microcontroller with suitable interfaces to the other components of the apparatus. Alternatively or additionally, at least some of the functions of the processor may be carried out by a special-purpose digital signal processor and/or by other digital logic, which may be hard-wired or programmable.

In the embodiments that are described below, processor 42 performs the functions described herein in conjunction with digital logic circuits that are integrated with SPAD array 36. The processor and the digital logic circuits are referred to collectively in the present description and in the claims as "processing circuitry." The processor itself is omitted from the figures that follow for the sake of simplicity. The structure and functionality of the digital logic circuits are described in greater detail in the above-mentioned U.S. patent application Ser. No. 18/623,080.

In the present embodiment, processor 42 counts the SPAD pulses that are output by receiver 24 as a function of time and uses these pulse counts both in producing 2D images of FOV 32 and to measure features of objects of interest, such as face 33, within the FOV. To produce the 2D images, processor 42 receives total counts of the electrical pulses output by each SPAD in array 36 during a given exposure time. To measure features, such as a 3D map of the face and/or blood vessels under the skin, processor 42 generates digital temporal waveforms defined by the counts of the pulses output by each pixel or group of pixels as a function of time in an area extending over face 33. Processor 42 extracts the beat frequencies from the digital temporal waveforms and uses the beat frequencies in measuring the features of the face.

In some embodiments, as noted above, transmitter 22 applies a frequency chirp to the FMCW radiation that is transmitted toward the scene. The processor then computes ranges of points on face 33 in the target scene based on the beat signals that arise due to the frequency chirp. Using up-chirp and down-chirp beat frequencies, the processor may also detect the Doppler shift of the reflected optical radiation and thus measure movements of the face (and/or of other objects in the FOV).

In another embodiment, the processor detects Doppler shifts in the beat signals that arise due to blood flow in blood vessels underneath the skin of the face, even without application of a frequency chirp. For this purpose, the transmitter projects FMCW infrared radiation toward the face, at a wavelength that penetrates through the skin but is reflected by blood cells. Blood cells flowing in the blood vessels with radial velocity components relative to the transmitter will cause Doppler shifts in the reflected radiation, which will give rise to beat signals at the pixels in the receiver onto which the blood vessels are imaged. By sensing these beat signals, the processor is able to identify and map the blood vessels.

Figure 2:
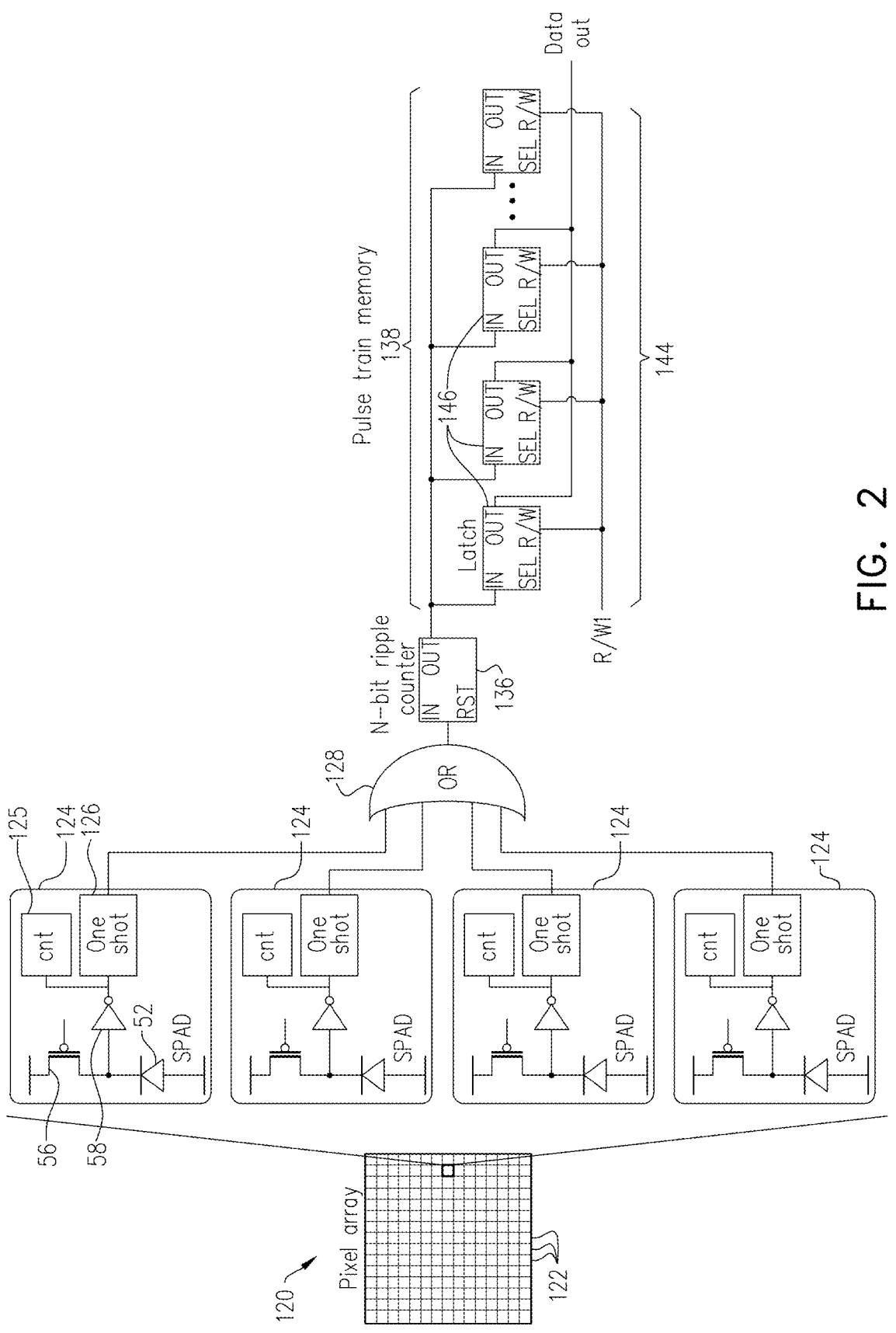
FIG. 2 is a block diagram showing details of an array of pixels comprising SPADs and associated circuitry, in accordance with another embodiment of the invention.

FIG. 2 is a block diagram that schematically illustrates an array 120 of pixels 124 comprising respective SPADs 52 and associated processing circuitry, in accordance with an alternative embodiment of the invention. This embodiment is suitable for use as a part of receiver 24 (FIG. 1). The processing circuitry enables the array to capture both 2D images and beat frequencies, either simultaneously or sequentially. Each SPAD 52 generates a corresponding pixel of the 2D image. For beat frequency extraction and associated 3D mapping, SPADs 52 are grouped into "superpixels" 122, each comprising four mutually adjacent SPADs. Alternatively, the superpixels may comprise larger or smaller numbers of SPADs.

Array 120 in this embodiment may advantageously comprise two chips, stacked one over the other: an upper chip containing SPADs 52 and a lower chip containing the associated logic circuits for each SPAD. The upper chip may be configured for back-side illumination (BSI) of the SPADs, i.e., with the back side of the chip facing outward, while the front side of this SPAD chip is bonded to the logic chip. The upper chip contains an array of SPADs with associated bias and quenching circuits, as shown in the inset. To conserve power, the bias may be switched on and off by a gate 56. For each SPAD 52, the logic chip in this example comprises an inverter 58 followed by a counter (cnt) 125, which counts the pulses output by the SPAD, and a one-shot pulse generator 126 to sharpen the electrical pulses that the SPAD outputs.

To generate a 2D image of the FOV of the receiver, processor 42 (FIG. 1) reads out the count values from counters 125 in all the pixels 124 in array 120. These count values provide the corresponding pixel values in the 2D image.

To sense FMCW beat signals, the pulse outputs from the four SPADs 52 making up a superpixel 122 are joined into a single pulse stream by an OR gate 128. The combined count values are input to a counting circuit 144, which comprises a ripple counter 136 and a pulse train memory 138. Ripple counter 136 counts the pulses in each of a sequence of time bins. The count values are clocked into pulse train memory 138, which comprises a series of bin buffers 146. The count values are clocked through bin buffers 146 over the sequence of time bins with a clock period equal to the temporal width of the bins. Counting circuit 144 accumulates count values in this manner over multiple sub-frames, wherein each sub-frame corresponds to the period of a single frequency chirp by the transmitter. Thus, at the end of the sub-frame, each bin buffer 146 stores the pulse count for this superpixel 122 in a respective time slot within the sub-frame. At the end of each sub-frame, pulse train memory 138 contains a digital temporal waveform with a duration equal to the chirp period and temporal resolution determined by the number of bins. Processor 42 reads the data out of the bins in parallel and processes the data to extract the beat frequency (or frequencies), as described below.

In an alternative embodiment (not shown in the figures), the pulse train memory for each superpixel 122 may comprise two parallel pulse train buffers, with a multiplexer that feeds the pulses output by the OR gate to the pulse train buffers in alternation over successive sub-frames. While one of the pulse train buffers is filled in the manner during a given sub-frame, the other pulse train buffer is read out and processed. This double-buffering scheme, which is described in detail in the above-mentioned U.S. patent application Ser. No. 18/623,080, is advantageous in achieving higher operating speed. On the other hand, the single-buffer scheme that is shown in FIG. 2 enables pulse counts to be collected with higher temporal resolution relative to the total amount of memory that is used. In applications that are not too time sensitive, such as face recognition, the single-buffer approach shown in FIG. 2 may be preferable for this reason.

Figure 4:
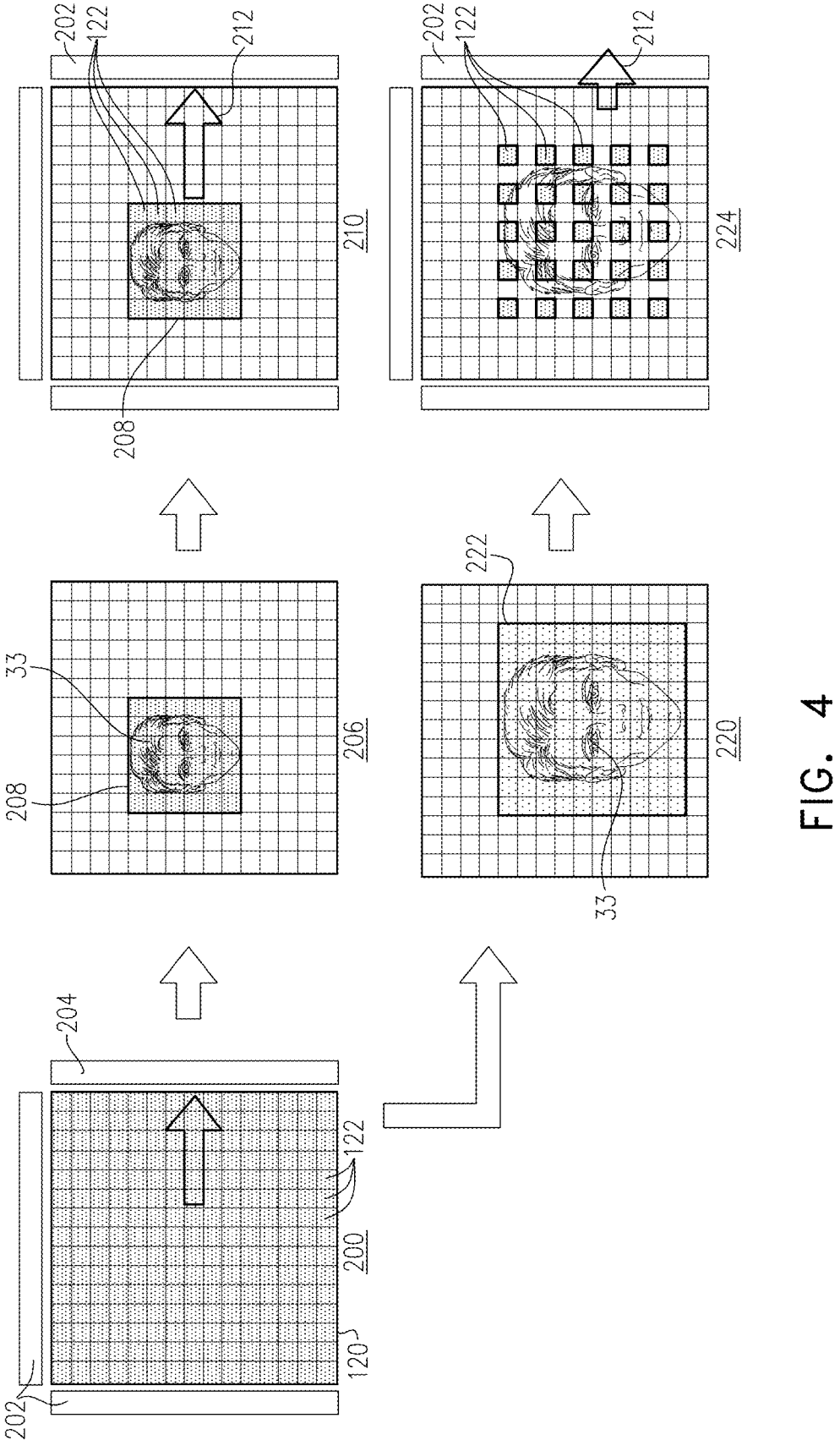
FIG. 4 is a flow diagram that schematically illustrates a method for identity verification, in accordance with an embodiment of the invention.

In some embodiments (for example, as illustrated in FIG. 4), to reduce the size and power consumption of the receiver, the number of counting circuits is substantially smaller than the number of superpixels 122 in array 120. In this case, the pulse trains that are output by OR gates 128 are routed selectively to the available counting circuits. For this purpose, processor 42 typically identifies an area of interest in the 2D image, for example an area that was found to contain a face, and only the outputs of the superpixels in this area are conveyed to the counting circuits. Alternatively, each superpixel may have its own, dedicated counting circuit, but only the pixels and counting circuits in the area of the interest are activated, while the remaining pixels and counting circuits are dormant to conserve power.

In an alternative embodiment, the individual counters 125 within each pixel 124 are eliminated from the logic chip to reduce the size and complexity of the pixel logic circuits. In this case, to collect the 2D image data with high spatial resolution, the four SPADs 52 in each superpixel 122 are actuated sequentially (for example by turning on the respective bias voltages at different times). The counting circuit is operated to give a single, cumulative count of all the pulses output by each SPAD during a respective frame, and these counts are then assembled to form a single, high-resolution 2D image.

Figure 3:
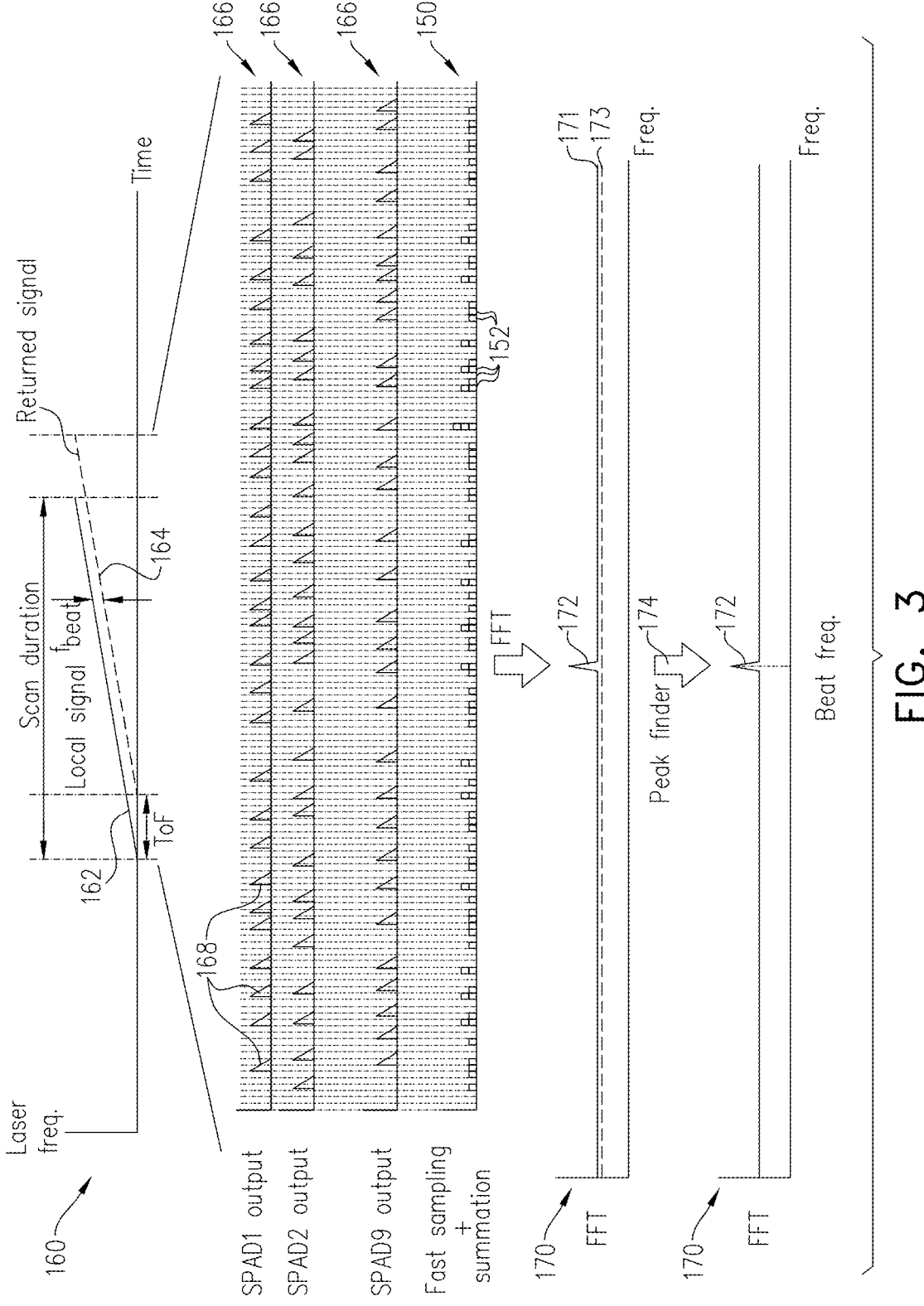
FIG. 3 is a timing diagram that schematically illustrates the operation of a single superpixel in the array of FIG. 2, in accordance with an embodiment of the invention.

FIG. 3 is a timing diagram that schematically illustrates the operation of a single superpixel 122 in array 120 (FIG. 2), in accordance with an embodiment of the invention. An upper plot 160 in the figure shows a frequency chirp 162 over time that is applied to the outgoing transmitted and local beams by transmitter 22 (FIG. 1), together with a corresponding delayed frequency chirp 164 of the incoming optical radiation that has been reflected from the target scene. The temporal offset between outgoing and incoming chirps 162 and 164 is equal to the time of flight (ToF) of the photons, and it gives rise to an optical beat signal at a frequency $f_{beat}$ that is equal to the instantaneous frequency difference between the outgoing and incoming radiation.

Each of the SPADs in a given superpixel group (labeled SPAD1, SPAD2, . . . , SPAD9) outputs a sequence 166 of pulses 168 in response to incident photons. Typically, most of the pulses are due to ambient light and will thus have a random distribution over time with a flat frequency spectrum 173. A small fraction of the pulses, however, will be due to the optical beating between the outgoing and incoming radiation and will give rise to a waveform 171 including a peak 172 in a frequency spectrum 170 at the beat frequency. To find this beat frequency, counting circuits 144 (FIG. 2) count the total number of pulses output by SPADs 52 in the superpixel group as a function of time and store the counts in corresponding time bins 152 in a buffer 150. The width of the bins is selected depending on the desired range resolution and may be 1 ns or less, for example. Counting circuits 144 output a digital temporal waveform defined by the sequence of count values over time in buffer 150.

To extract the beat frequency at each superpixel, processor 42 (FIG. 1) converts the temporal waveform to the frequency domain, for example by computing a fast Fourier transform (FFT) over the waveform, giving frequency spectrum 170. Processor 42 then applies a peak-finding algorithm 174 to find the frequency bin with the maximum amplitude. Processor 42 verifies that the shape of this peak 172 in the frequency domain matches the expected shape of the beat signal, for example using a matching filter. Processor 42 converts this frequency to a range value for the corresponding spot location in the target scene. In some cases, multiple peaks may be found. Furthermore, although FIG. 6 shows only a single, upward frequency chirp 162, transmitter 102 may alternatively apply a down-chirp as well to enable the processor to find target scene velocities, as well.

Identity Verification Using Multi-Modal Face Recognition

FIG. 4 is a flow diagram that schematically illustrates a method for identity verification using the system described above, in accordance with an embodiment of the invention. In this method, processor 42 (FIG. 1) identifies face 33 in the 2D image that is output by receiver 24 and then generates a 3D map of the face based on the beat frequencies generated by superpixels 122 in the area of the 2D image that contains the face. The 3D map can be applied in verifying the identity of the person whose face appears in the 2D image.

In an initial stage 200, apparatus 20 (FIG. 1) acquires a 2D image of FOV 32 of receiver 24 by reading out the count values from all the pixels in array 120, as described above. For this purpose, selection logic 202 transfers the count values sequentially to a readout circuit 204. In face identification stages 206 and 220, processor 42 applies methods of face identification that are known in the art to find face 33 in the 2D image. Depending on the distance of the face from the sensing apparatus, face 33 may be imaged onto a small area 208 of array 120, shown in stage 206, or onto a larger area 222, in stage 220. For purposes of authentication, processor 42 may apply methods of face recognition that are known in the art to ascertain the identity of the person whose face appears in the 2D image.

In stages 210 and 224, processor 42 defines a region of interest (ROI), for example in the form of a bounding box that contains the area 208 or 222 of array 120 in which face 33 was identified. The processing circuitry counts the pulses that are output as a function of time from superpixels 122 within the ROI. Processor 42 extracts beat frequencies 212 from the digital waveforms defined by the counts and thus computes a depth coordinate for each superpixel 122. Alternatively or additionally, the processor may extract velocity information from the beat signals. Processor 42 actuates and reads out the counts only from SPADs 52 (FIG. 2) within the ROI, while disabling or otherwise ignoring the remainder of the SPAD array outside the box. When the ROI is not too large, as in stage 210, the processor may actuate all the superpixels within the ROI. When the ROI is too large, meaning that there are more superpixels 122 in the ROI than counting circuits available to receive their respective counts, the processing circuitry may sub-sample the superpixels within the ROI, as shown in stage 224.

In either case, once processor 42 has completed its analysis of the beat signals, it uses the resulting depth and/or velocity information in verifying that the measured depth and/or other features match the identity of the person whose face appears in the 2D image.

The embodiments described above are cited by way of example, and the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Optical sensing apparatus, comprising:
a transmitter, which is configured to transmit outgoing frequency-modulated (FM) coherent optical radiation toward a target scene;
a receiver, comprising:
an array of detectors, which are configured to output electrical signals in response to photons that are incident on the detectors, wherein the detectors are single-photon detectors, which are configured to output electrical pulses in response to the incident photons; and
optics configured to image the target scene onto the array while diverting a part of the outgoing FM coherent optical radiation to form a local beam, which mixes with incoming optical radiation from the target scene; and
processing circuitry configured to process the electrical signals output by the detectors to produce a two-dimensional (2D) image of the target scene, to identify an object of interest in the 2D image, which is imaged onto an area within the array, to extract beat frequencies in response to the mixed optical radiation from the electrical signals output by the detectors in the area, and to measure a three-dimensional feature of the object of interest responsively to the beat frequencies,
wherein the processing circuitry is configured to compute counts of the electrical pulses output as a function of time by the single-photon detectors, wherein the counts of the electrical pulses as the function of time define temporal waveforms, and wherein the processing circuitry is configured to extract the beat frequencies by processing the temporal waveforms.

2. The apparatus according to claim 1, wherein the transmitter is configured to project the FM coherent optical radiation as flood radiation over a region of the target scene.

3. The apparatus according to claim 1, wherein the processing circuitry is configured to produce the 2D image responsively to total counts of the electrical pulses output by each of the single-photon detectors during a given exposure time.

4. The apparatus according to claim 1, wherein the processing circuitry is configured to select groups of the single-photon detectors within the area and to compute the counts as collective counts of the electrical pulses output by each of the selected groups of the single-photon detectors.

5. The apparatus according to claim 1, wherein the single-photon detectors comprise single-photon avalanche diodes (SPADs).

6. The apparatus according to claim 1, wherein the transmitter is configured to apply a frequency chirp to the outgoing coherent optical radiation, and the processing circuitry is configured to measure a three-dimensional shape of the object of interest based on the beat signals that arise due to the frequency chirp.

7. The apparatus according to claim 1, wherein the processing circuitry is configured to detect, based on the beat signals, a Doppler shift indicative of movement of a feature of the object of interest.

8. The apparatus according to claim 7, wherein the object of interest is a part of a living body, and wherein the processing circuitry is configured to detect the Doppler shift due to flow of blood in blood vessels in the living body and to identify the blood vessels responsively to the detected Doppler shift.

9. The apparatus according to claim 1, wherein the processing circuitry is configured to identify a face in the 2D image and to generate a three-dimensional (3D) map of the face based on the beat frequencies.

10. The apparatus according to claim 9, wherein the processing circuitry is configured to apply the 3D map in verifying an identity of a person whose face appears in the 2D image.

11. A method for optical sensing, comprising:
transmitting outgoing frequency-modulated (FM) coherent optical radiation toward a target scene;
imaging the target scene onto an array of detectors, which output electrical signals in response to photons that are incident on the detectors, while diverting a part of the outgoing FM coherent optical radiation to form a local beam, which mixes on the array of detectors with incoming optical radiation from the target scene, wherein the detectors are single-photon detectors, which are configured to output electrical pulses in response to the incident photons;
processing the electrical signals output by the detectors to produce a two-dimensional (2D) image of the target scene;
identifying an object of interest, which is imaged onto an area within the array, in the 2D image;
extracting beat frequencies in response to the mixed optical radiation from the electrical signals output by the detectors in the area,
wherein extracting the beat frequencies comprises computing counts of the electrical pulses output as a function of time by the single-photon detectors, wherein the counts of the electrical pulses as the function of time define temporal waveforms, and wherein the beat frequencies are extracted by processing the temporal waveforms; and
measuring a three-dimensional feature of the object of interest responsively to the beat frequencies.

12. The method according to claim 11, wherein the transmitting the outgoing FM coherent optical radiation comprises projecting the FM coherent optical radiation as flood radiation over a region of the target scene.

13. The method according to claim 11, wherein processing the electrical signals comprises producing the 2D image responsively to total counts of the electrical pulses output by each of the single-photon detectors during a given exposure time.

14. The method according to claim 11, wherein transmitting the outgoing FM coherent optical radiation comprises applying a frequency chirp to the outgoing coherent optical radiation, and wherein measuring the feature comprises measuring a three-dimensional shape of the object of interest based on the beat signals that arise due to the frequency chirp.

15. The method according to claim 11, wherein extracting the beat frequencies comprises detecting, based on the beat signals, a Doppler shift indicative of movement of a feature of the object of interest.

16. The method according to claim 15, wherein the object of interest is a part of a living body, and wherein detecting the Doppler shift comprises sensing a flow of blood in blood vessels in the living body and identifying the blood vessels responsively to the detected Doppler shift.

17. The method according to claim 11, wherein identifying the object of interest comprises identifying a face in the 2D image, and wherein measuring the feature comprises generating a three-dimensional (3D) map of the face based on the beat frequencies.

* * * * *